United States Patent [19]

Onishi et al.

[11] Patent Number: 5,503,631
[45] Date of Patent: Apr. 2, 1996

[54] LUBRICIOUS CATHETER BALLOON FOR VASODILATION

[75] Inventors: Makoto Onishi, Kanagawa; Kenichi Shimura, Tokyo, both of Japan

[73] Assignee: Terumo Kabushiki Kaisha, Tokyo, Japan

[21] Appl. No.: 132,873

[22] Filed: Oct. 7, 1993

[30] Foreign Application Priority Data

Oct. 9, 1992 [JP] Japan ................... 4-271436

[51] Int. Cl.$^6$ .................................... A61H 29/00
[52] U.S. Cl. ........................... 604/96; 606/194
[58] Field of Search ................... 604/96, 265, 266; 606/191, 192, 194

[56] References Cited

U.S. PATENT DOCUMENTS

| 3,726,281 | 4/1973 | Norton et al. | |
| 3,962,519 | 6/1976 | Rusch et al. | |
| 4,100,309 | 7/1978 | Micklus et al. | 427/2 |
| 4,248,685 | 2/1981 | Beede et al. | 204/159 |
| 4,373,009 | 2/1983 | Winn | 428/424.2 |
| 4,876,126 | 10/1989 | Takemura et al. | 428/35.7 |
| 4,998,923 | 3/1991 | Samson et al. | 606/194 |
| 5,091,205 | 2/1992 | Fan | 427/2 |
| 5,108,416 | 4/1992 | Ryan et al. | 606/194 |
| 5,135,516 | 8/1992 | Sahatjian et al. | 604/265 |
| 5,270,086 | 12/1993 | Hamlin | 428/35.2 |
| 5,278,200 | 1/1994 | Coury et al. | 523/112 |
| 5,304,121 | 4/1994 | Sahatjian | 604/53 |
| 5,338,298 | 8/1994 | McIntyre | 604/96 |
| 5,397,305 | 3/1995 | Kawula et al. | 604/96 |
| 5,423,754 | 6/1995 | Cornelius et al. | 604/103 |

FOREIGN PATENT DOCUMENTS 0311427  4/1989  European Pat. Off. .

*Primary Examiner*—Corrine McDermott
*Attorney, Agent, or Firm*—Burns, Doane, Swecker & Mathis

[57] ABSTRACT

A vasodilating catheter balloon characterized by the fact that the balloon portion thereof is provided with what serves concurrently as a lubricating portion and a non-lubricating portion.

9 Claims, 3 Drawing Sheets

LUBRICIOUS CATHETER BALLOON FOR VASODILATION

BACKGROUND OF THE INVENTION

1. Field of the Invention

This invention relates to a catheter balloon for use in vasodilation. More particularly, it relates to a catheter balloon for vasodilation characterized by the fact that the balloon part of the vasodilating catheter balloon is provided with what concurrently serves as a lubricating portion and as a non-lubricating portion.

2. Description of the Prior Art

Generally, obvious signs of adhesion such as of blood clot, loose tissue, fragments from injured tissue, and products of extraneous reactions are observed frequently on the surfaces of substrates of medical tools and devices. For the purpose of minimizing these adverse phenomena, the practice of using materials of low friction for such substrates and the practice of coating the surfaces of such substrates with a hydrophilic polymer have been in vogue. Particularly, in the case of such medical tools as catheters which by nature are used as inserted in body cavities and blood vessels, since the alleviation of the resistance offered by the tools during the insertion thereof into body cavities results in preventing the tools from injuring the tissue and improving the operability of the tools, it is important to impart lubricity to the surfaces of such tools. For example, the practice of adopting substances of low friction like fluorine resin and polyethylene as materials for these medical tools and the practice of coating the surfaces of substrates with fluorine resin, silicone oil, olive oil, and glycerol are now prevailing. The method of coating, however, fails to provide lasting lubricity as desired, entails the problem of fallibility in respect that the applied coats of lubricating substances will easily depart, peel, or dissolve from the surfaces of substrates, and proves to be unbeneficial for medical tools.

JP-A-59-81,341 discloses a method for enabling the surface of a medical tool to manifest necessary lubricity by causing the unaltered isocyanate group on the surface to react with a hydrophilic polymer capable of forming a covalent bond with the isocyanate group. Since the hydrophilic polymer has N-vinyl-2-pyrrolidone as a main component thereof, for example, this method is at a disadvantage in respect that the lubricating layer to be formed thereby has too low strength to ensure manifestation of the lasting durability which is indispensable for repeated use of the coated medical tool. Thus, this method proves to be unbeneficial for medical tools. U.S. Pat. No. 4,100,309 has a disclosure to the effect that a copolymer of polyvinyl pyrrolidone with polyurethane is used as a substance possessing lubricity. The method taught by this invention indeed is satisfactory in terms of lubricity and lasting durability. When the copolymer is used on the surface of a balloon in the vasodilating catheter balloon which is one of medical tools, the coated balloon exhibits an excellent operability during the insertion thereof into a body cavity. When the coated balloon is inflated at a site selected for blockage in the blood vessel, however, the poor resistance of the surface of this balloon due to excessively high lubricity thereof often entails accidental slippage of the balloon from the target site (such as, for example, a site affected by stenosis) and renders the therapy difficult.

JP-B-1-33,181 discloses a method for imparting lubricity to the surface of a substrate forming a medical tool while the surface is in a state by causing a reactive functional group present in the surface to react with a maleic anhydride type polymeric material. Again this method is at a disadvantage in not ensuring safe retention of the treated substrate at the target site.

As described above, the conventional vasodilating catheter balloon possessing lubricity is handicapped by fallibility of retention of the balloon at the target site notwithstanding the excellent operability exhibited during the insertion thereof in a body cavity.

An object of this invention, therefore, is to provide a novel vasodilating catheter balloon.

Another object of this invention is to provide a vasodilating catheter balloon which is liberated from the various problems mentioned above and enabled to fulfill simultaneously high operability during the insertion into a body cavity and infallible retention of the balloon at the target site.

SUMMARY OF THE INVENTION

These objects are accomplished by a vasodilating catheter balloon characterized by the fact that the balloon portion thereof is provided with what serves concurrently as a lubricating portion and a non-lubricating portion.

This invention further pertains to a vasodilating catheter balloon so constructed that the lubricating portion is formed in a tapered portion of the balloon portion thereof.

Since the vasodilating catheter balloon of this invention is provided with what concurrently serves as a lubricating portion and a non-lubricating portion, it not merely facilitates the insertion of the catheter balloon into a body cavity or the manipulation thereof in the target site but also renders the retention of the balloon part thereof at the target site easy.

DESCRIPTION OF THE PREFERRED EMBODIMENT

Figure 1:
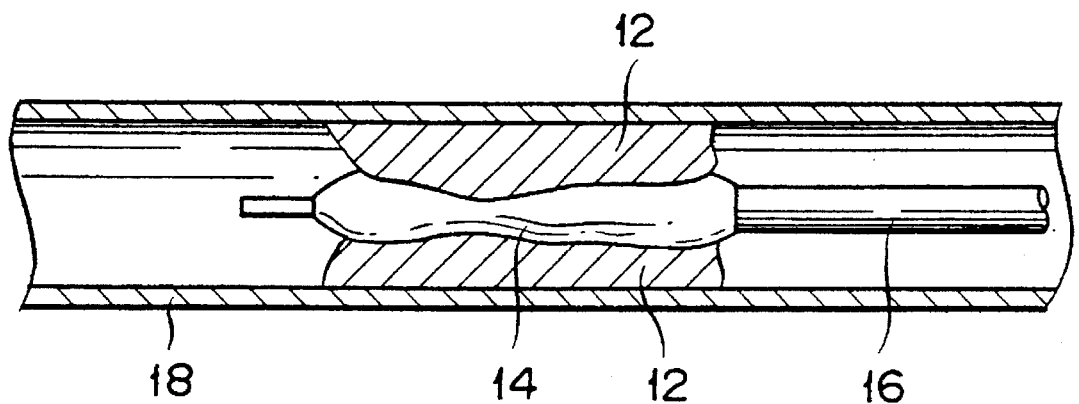
FIGS. 1 and 2 are schematic cross sections illustrating a method for using a vasodilating catheter.
Figure 2:
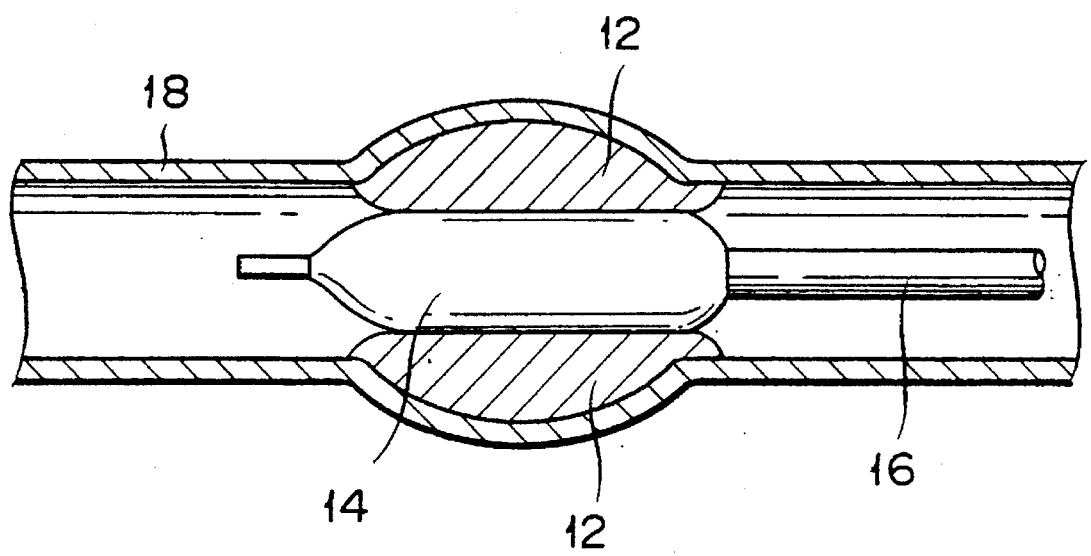

The term "vasodilating catheter" as used in this invention means a catheter 16 which, as illustrated in Figs. 1 and 2, is provided with a balloon 14 for dilating the interior of a blood vessel 18 at the portion affected by blockage or stenosis 12. The use of this vasodilating catheter is attained by inserting the catheter 16 into the blood vessel 18, advancing the catheter 16 through the blood vessel to a target site (part of the blood vessel affected by blockage or stenosis) 12, and then injecting a radiopaque substance for angiography into the catheter 16 now located at the target site 12 thereby inflating the balloon 14 and expanding the target site 12 and eliminating the blockage or stenosis. During the insertion of the catheter 16 in the blood vessel 18 or the advance thereof through the blood vessel 18 to the target site 12, therefore, the catheter 16 is operated more easily when the surface of the catheter 16 and particularly that of the balloon possesses lubricity. During the contraction or expansion of the target site, the inflated balloon is retained more easily at the target site when the surface of the balloon has no lubricity because the inflated balloon fails to move from the target site in the absence of lubricity.

The lubricating part, therefore, is only required to be formed at a position at which the catheter offers resistance to the insertion thereof into the blood vessel. The shape of the lubricating portion has no particular restriction. Generally, since the balloon is inserted in a folded state into the blood vessel, the lubricating portion is desired to be located either in the part of the folded balloon which remains in contact with the inner wall of the blood vessel or in the tapered part of the balloon, preferably the tapered part on the leading end side of the balloon, which is liable to form a cause for friction during the insertion.

The term "lubricating portion" as used in this invention means a portion which is formed of a polymeric substance capable of being swelled or dissolved with water to be absorbed. The polymeric substance has no particular restriction except for the requirement that it should manifest low friction in such humoral fluids as saliva, digestive fluid, and blood and in such aqueous solvents as physiological saline solution and water. As typical examples of the polymeric substance, maleic anhydride type polymeric substances, acryl amide type polymeric substances, and polysaccharides may be cited.

As a maleic anhydride type polymeric substance, though the homopolymer of maleic anhydride may be used satisfactorily, particularly a methylvinyl ether-maleic anhydride copolymer is used ideally. As a typical example of the copolymer, a copolymer composed of the comonomers substantially at a ratio of 1:1 (a product of G. A. F. Corporation marketed under trademark designation of "Gantrez AN") may be cited. The derivatives of maleic anhydride type polymeric substances are not limited to those of the type which are soluble in water. Those of the type which have a maleic anhydride type polymeric substance as a basic construction and are capable of manifesting lubricity while in a wet state are counted among the derivatives under discussion even when they are in an insolubilized form.

As respects the acryl amide type polymeric substances, polymers having N,N-dimethyl acryl amide as a main component thereof prove to be desirable typical examples in the light of such factors as operability, safety, and economy.

As typical examples of the polysaccharides which manifest lubricity while in a wet state, hyaluronic acid, chondroitin, chondroitin sulfuric acid, kerantosulfuric acid, kerantopoly-sulfuric acid, heparanic acid, and mucopolysaccharides, i.e. salts of such acids which occur predominantly in animal tissues and humoral fluids and alginic acid and salts thereof which are generally consumed by human beings may be cited. These polysaccharides are highly desirable because they can be expected to ensure high safety when they are used on medical tools.

A polymeric substance which is swelled or dissolved with absorbed water has too small mechanical strength to be used directly as a substrate for a medical tool. The direct use of this substance as the substrate is undesirable further in terms of safety. Generally, it is desirable to use a hydrophobic polymeric substance having high mechanical strength as a substrate and fix this polymeric substance by a chemical treatment. Virtually any method may be used for the fixation of the hydrophobic polymeric substance by a chemical treatment on the condition that the surface of the substrate should show no discernible sign of exudation or separation.

The method of surface graft polymerization proves to be desirable in the light of operability and safety.

The methods which are available for the impartation of hydrophilicity to the surface of a hydrophobic polymeric material by a grafting treatment are broadly classified under the following three types.

(1) Light-ultraviolet light method
(2) Radiation graft method
(3) Glow-discharge (plasma) graft method The light-ultraviolet light method attains synthesis of a graft polymer by generating graft reaction points (radicals) on the surface of a material by the use of a photosensitizer or a polymeric substance possessing a light absorbing group and supplying a polymerizing monomer of a different species by virtue of the radicals. Since the photosensitizer or the polymeric substance possessing a light absorbing group generally has high toxicity, it is not very desirable to use such toxic substance on medical tools.

The radiation graft method comprises breaking such a covalent bond as a C—H bond by the irradiation with a y ray or a neutron ray and attaining necessary grafting by virtue of the radicals to be consequently formed. In this method, the grafting initially proceeds exclusively on the surface of a polymeric substance being used as a substrate and the diffusion of a polymerizing monomer in the polymer of the substrate constitutes itself a rate controlling factor for the grafting. Then, as the grafting proceeds and consequently the crystal structure of the substrate grows loose, the diffusion of the polymerizing monomer in the polymer gains in speed and the internal grafting proceeds likewise. This method, therefore, is unsuitable for selective modification of the surface of the substrate because it has the possibility of jeopardizing the physical properties of the substrate. Further, since this method uses a y ray or a neutron ray and, therefore, necessitates a special apparatus, it is at a disadvantage in not enabling just anyone to use the method freely.

The glow-discharge (plasma) graft method, just like the radiation graft method, comprises breaking such covalent bond as a C—H bond by the irradiation with plasma and then effecting necessary grafting by virtue of the radicals to be consequently formed. The radicals are formed mainly in the veritably surface region of the substrate and the grafting proceeds in the interior of the substrate with difficulty. This method causes only small alteration of attributes and properties of the substrate and effects modification of only the surface of the substrate and, therefore, excels the radiation graft method in terms of operability and economy.

The term "non-lubricating portion" as used in this invention means the part capable of producing resistance to extraction for the sake of retaining the balloon at the target site (part affected by blockage or stenosis) in the body. This portion is formed of a polymeric substance which possesses no surface lubricity (or abounds in friction). As particularly desirable typical examples of the polymeric substance, polyethylene terephthalate, nylon, polyolefins, cross-linked polyolefins, and polyphenylene sulfide may be cited. These polymeric substances, when desired, may be used in the form of shaped articles and multilayered articles of alloyed masses of such substances.

This invention imposes no particular restriction on the method which is to be used for the fabrication of the lubricating portion and non-lubricating portion on the balloon component of the vasodilating catheter balloon. With respect to such factors as economy, workability, and operability, however, it is desirable to effect this fabrication by preparing a balloon substrate with a polymeric material having no surface lubricity (abounding in friction) and partially coating the pertinent surface of the balloon substrate through the medium of a proper masking with a polymeric material possessing surface lubricity by such method of fixation as the aforementioned plasma graft method.

The balloon 14 which is formed as described above is attached as illustrated in FIGS. 3 and 4 to a vasodilating catheter 40. The vasodilating catheter 40 of this invention which is provided at the leading end thereof with the balloon is composed of an inner tube 1, an outer tube 2, and a balloon 14 as-illustrated in FIGS. 3 and 4.

The inner tube 1 is provided with a first lumen 4 which opens in the leading end thereof. This first lumen 4 serves the purpose of allowing insertion therethrough of a guide wire.

Figure 4:
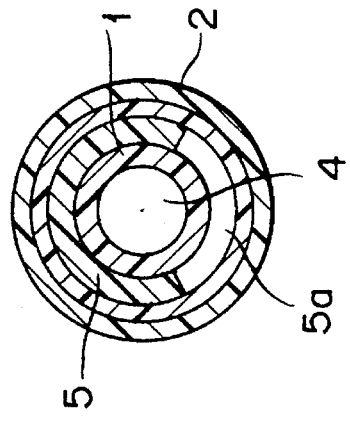
FIG. 4 is a cross section taken through FIG. 3 along the line IV—IV.

The outer tube 2 has the inner tube 1 inserted therein in such a manner that the leading end thereof occupies a position slightly behind that of the leading end of the inner tube. The inner surface of the outer tube 2 and the outer surface of the inner tube 1 define a second lumen 6. The second lumen 6 is adapted to communicate via the leading end thereof with a balloon 14 which will be described more specifically hereinafter via the training end portion thereof so as to allow flow of a fluid (such as, for example, a radiopaque substance for angiography) to be used for inflating the balloon 14. The leading end part of the outer tube 2 is fixed to the inner tube 1 in such a manner as to avoid blocking the second lumen 6. Specifically, this fixation is effected with a filling agent 5 which is disposed between the outer tube 2 and the inner tube 1 as illustrated in FIG. 4. This filling agent 5 is provided with a partially missing part 5a. This missing part 5a establishes communication between the second lumen 6 with the interior of the balloon 14.

The balloon 14 is foldable. In the state not inflated, it is folded over itself on the outer surface of the inner tube 1. The balloon 14 is provided with an approximately cylindrical part which at least partially assumes a generally cylindrical shape so as to facilitate inflation of a portion of stenosis in the blood vessel. The balloon 14 has a trailing end portion 8 thereof fixed watertightly to the leading end part of the outer tube 2 and a leading end portion 7 thereof fixed watertightly to the leading end portion of the inner tube 1. An expansion empty space 15 is formed between the inner surface of the balloon 14 and the outer surface of the inner tube 1. The expansion empty space 15 communicates via the trailing end part thereof with the second lumen 6 through the medium of the missing part 5a of the filling agent 5.

The inner tube 1 is provided on the outer surface thereof with a reinforcing member 30. This reinforcing member 30 is formed of a coil spring and is located, for the purpose of permitting easy detection of the position of the balloon 14 under X-ray radiographic examination, on the outer surface of the inner tube 1 near the center of the balloon 14 and the outer surface of the inner tube 1 near the tapered part of the balloon 14 (near the leading end portion of the outer tube 2).

Concerning the material for the inner and outer tube, it may be of virtually any kind and may be in the form of a simple substance or a mixture of two or more substances. As examples of the material, polyvinyl chloride, polyethylene, polypropylene, and a mixture of polypropylene with polybutene may be cited. Further, concerning the shape of the inner and outer tube, the substrate may be in a monolayer or a multilayer.

Now, this invention will be described more specifically below with reference to working examples. Further, adhesion of the balloon 14 with the outer tube 2 is carried out by heat melting or using an adhesive agent such as an epoxy resin, a cyanoacrylate adhesive, etc., and as the filling agent 5, although it may be different depending on the materials of the inner tube 1 and outer tube 2, when both the inner tube 1 and the outer tube 2 are made by a olefinic material, EVA (ethylene-vinyl acetate copolymer) is preferably used.

EXAMPLE 1

A balloon 14 was produced by biaxially stretching a modified polyethylene (produced by Mitsubishi Petrochemical Co., Ltd. and marketed under product code of "SF230") and an inner tube 1 and an outer tube 2 (hereinafter referred to "tubes") were produced by biaxially kneading 30 parts by weight of polypropylene (produced by Mitsui Petrochemical Industries, Ltd. and marketed under trademark designation of "Hipole F401") and 70 parts by weight of polybutene (produced by Mitsui Petrochemical Industries, Ltd. and marketed under trademark designation of "Puron").

Figure 3:
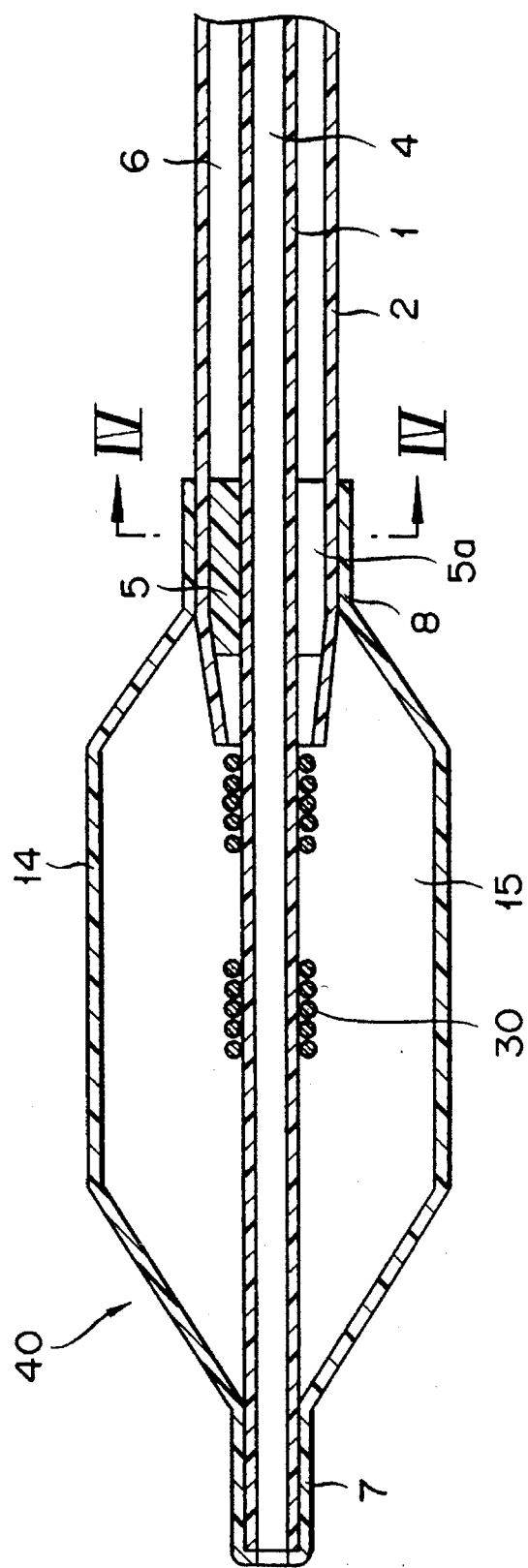
FIG. 3 is a longitudinal cross section of a vasodilating catheter using a balloon according with this invention.

Only the tapered portions in the opposite ends of the balloon were exposed through proper masks to a low-temperature plasma (Ar, 0.1 torr) for 10 seconds and N,N-dimethyl acryl amide was graft polymerized on the treated surface portions at a temperature of 288K for ten minutes. This balloon 14 was attached to the tubes as illustrated in FIGS. 3 and 4.

Figure 5:
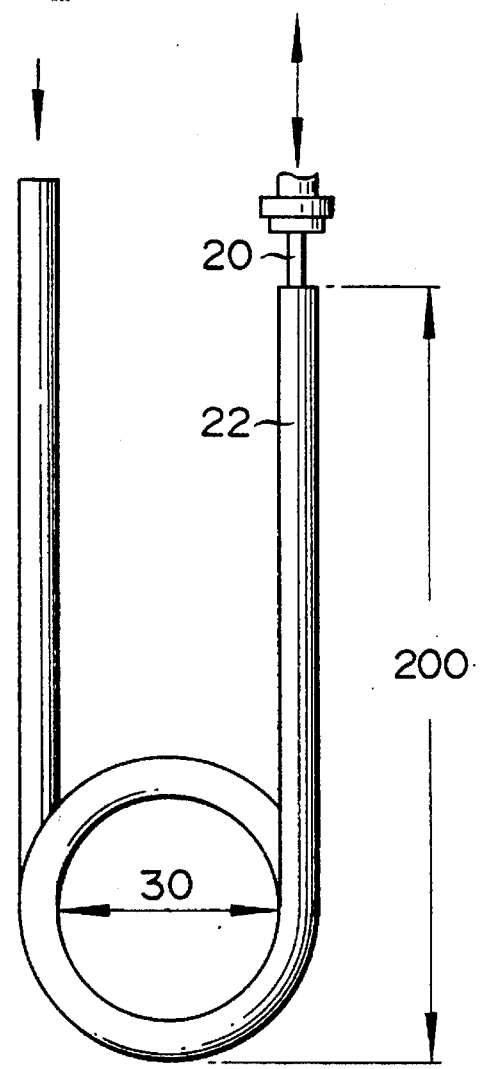
FIG. 5 is a schematic diagram illustrating a device for testing a balloon for lubricity (resistance to friction)

With a polyethylene pipe 22 having an inside diameter of 3 mm and an outside diameter of 5 mm, a flow path containing a spiral part consisting of one circle and a half 30 mm in inside diameter was shaped to simulate a blood vessel system in a living body as illustrated in FIG. 5. The pipe forming the flow path was filled with water. The balloon 14 was attached fast to the tube and, in a folded state, inserted into the pipe and set in place so that the leading part of the balloon would occupy a position at which the spiral part terminated. Then, the leading end part of the balloon 14 was reciprocated over a distance of 10 mm inside the pipe and the resistance offered by the reciprocation of the balloon was measured with an instrument (produced by Shimadzu Seisakusho Ltd. and marketed under trademark designation of "Autograph AGS-100") (not shown) under the following conditions.

Conditions of Measurement

Full scale: 5 kgf

Length of stroke: 10 mm

Speed of stroke: 100 mm/min

Number of strokes: 100

The magnitude of resistance which was found immediately after completion of the last of the 100 strokes was adopted as the value of friction resistance of the material tested.

Figure 6:
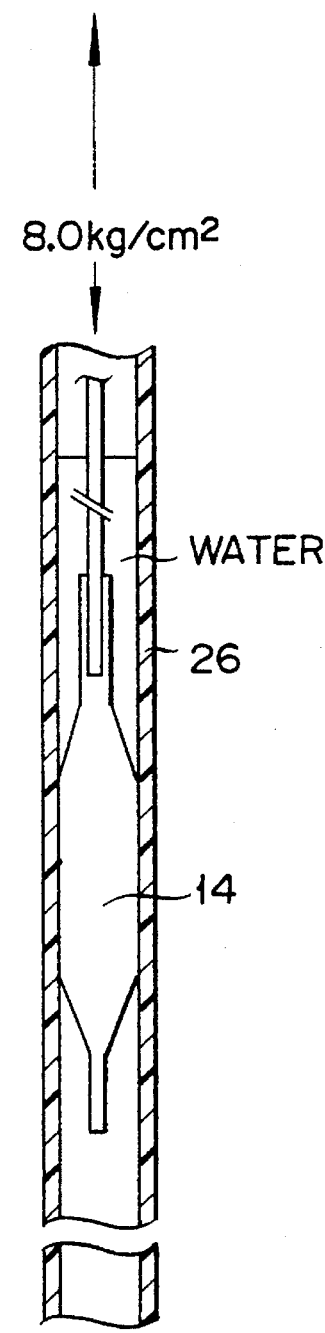
FIG. 6 is a schematic cross section illustrating a device for testing a balloon for ability to be retained (resistance to extracting force).

Then, in a flow path formed of a polyethylene pipe 26 having an inside diameter of 3 mm and an outside diameter 5 mm and filled with water as illustrated in FIG. 6, a balloon 14 attached to a tube and kept in a folded state was inserted so that the leading end part of the balloon 14 would occupy a position about 50 mm from the inlet of the pipe 26. Subsequently, the balloon 14 was inflated inside the pipe with a pressure of 8 kg/cm$^2$. The balloon 14 in the inflated state was extracted from within the pipe 26 and the magnitude of resistance offered by tube to the extraction was measured with an instrument (produced by Shimadzu Seisakusho Ltd. and marketed under trademark designation of "Autograph AGS-100") (not shown) under the following conditions.

Conditions of Measurement

Full scale: 5 kgf

Speed of extraction: 100 mm/min

The maximum magnitude of resistance offered during the extraction was adopted as the value of resistance to extraction of the material under test.

The results are shown in Table 1.

Control 1

A balloon catheter was obtained by following the procedure of Example 1, except that the balloon prepared first was not given any surface treatment prior to the attachment thereof to the tube. It was tested for friction resistance and for resistance to extraction by the methods depicted in FIGS. 5 and 6. The results are shown in Table 1.

Control 2

A balloon catheter was obtained by following the procedure of Example 1, except that the entire surface of the balloon was subjected to the surface treatment without use of any masking. It was tested for friction resistance and for resistance to extraction by the methods depicted in FIGS. 5 and 6. The results are shown in Table 1.

TABLE 1

| Sample No. | Surface treatment | Graft chain | Grafting ratio[1] | Friction resistance (gf)[2] | Resistance to extraction (gf)[3] |
| --- | --- | --- | --- | --- | --- |
| Example 1 | Partial treatment | Dimethyl acryl amide | 0.9 | 12.1 | 403 |
| Control 1 | None | None | — | 22.4 | 466 |
| Control 2 | Whole treatment | Dimethyl acryl amide | 1.7 | 10.3 | 235 |

[1]Amount of polymer bound per unit weight of substrate, expressed in terms of percent by weight.
[2]Value of resistance obtained immediately after completion of the last of a total of 100 strokes.
[3]Highest value of resistance found during extraction.

EXAMPLE 2

A balloon was obtained by biaxially stretching nylon (produced by Mitsubishi Gas Chemical Industries Ltd. and marketed under product code of "MXD-6121"). The tapered portion on the leading end side of this balloon was immersed for 10 seconds in a 1/10 mixture of hexafluoroisopropyl alcohol/ethyl acetate, then irradiated for 10 seconds with a low-temperature plasma (At, 0.1 torr), and subjected to a surface graft polymerization of methacryloyl oxyethyl isocyanate for 20 minutes at a temperature of 288K. The surface grafted balloon was immersed for ten seconds at normal room temperature in a tetrahydrofuran solution containing two parts by weight of methylvinyl ether-maleic anhydride copolymer (produced by Gantrez AN G. A. F. Corporation) and dried at 50° C. for a whole day and night. The dried balloon was neutralized with a physiological saline solution containing sodium hydrogen carbonate at 50° C. for three hours to obtain a sample. A balloon catheter was produced by attaching the balloon to a tube as illustrated in FIGS. 3 and 4 and tested for friction resistance and resistance to extraction by the methods depicted in FIGS. 5 and 6 under the same conditions as used in Example 1. The results are shown in Table 2.

Control 3

A balloon catheter was obtained by following the procedure of Example 2, except that the balloon was not given any surface treatment prior to the attachment thereof to the tube. This balloon was tested for friction resistance and resistance to extraction by the methods depicted in FIGS. 5 and 6. The results are shown in Table 2.

Control 4

A balloon catheter was obtained by following the procedure of Example 2, except that the entire surface of the balloon part was subjected without any masking to the same surface treatment as in Example 2. The balloon catheter was tested for friction resistance and resistance to extraction by the methods depicted in FIGS. 5 and 6. The results are shown in Table 2.

TABLE 2

| Sample No. | Surface treatment | Covering ratio[1] | Friction resistance (gf)[2] | Resistance to extraction (gf)[3] |
| --- | --- | --- | --- | --- |
| Example 2 | Partial treatment | 2.6 | 9.5 | 385 |
| Control 3 | None | — | 18.5 | 477 |
| Control 4 | Whole treatment | 4.2 | 8.8 | 233 |

[1]Amount or polymer bound per unit weight of substrate, expressed in terms of percent by weight.
[2]Value of resistance obtained immediately after completion of the last of a total of 100 strokes.
[3]Highest value of resistance found during extraction.

EXAMPLE 3

A balloon shaped as illustrated in FIG. 1 was obtained by biaxially stretching polyethylene terephthalate (produced by Nippon Unipet K.K. and marketed under trademark designation of "Unipet RN-165"). Only the tapered part on the leading end side of this balloon was immersed in toluene or dichloromethane, then irradiated for ten seconds with a low-temperature plasma (Ar, 0.1 torr), and subjected to 30 minutes' surface graft polymerization with glycidyl acrylate at a temperature of 288K. The surface grafted balloon was immersed for ten seconds at normal room temperature in a tetrahydrofuran solution containing two parts by weight of methylvinyl ether-maleic anhydride copolymer (produced by Gantrez AN G. A. F. Corporation) and dried at 60° C. for a whole day and night. The dried balloon was neutralized with a physiological saline solution containing sodium hydrogen carbonate at 50° C. for three hours to obtain a sample.

A balloon catheter was obtained by attaching the balloon to a tube as illustrated in FIGS. 3 and 4. With an instrument (produced by Shimadzu Seisakusho Ltd. and marketed under trademark designation of "Autograph AGS-100A"), the balloon catheter was tested for friction resistance and resistance to extraction by the methods depicted in FIGS. 5 and 6 under the same conditions as those of Example 1. The results are shown in Table 3.

Control 5

A balloon catheter was obtained by following the procedure of Example 3, except that the balloon was not given any surface treatment prior to the attachment thereof to the tube. This balloon was tested for friction resistance and resistance to extraction by the methods depicted in FIGS. 5 and 6. The results are shown in Table 3.

Control 6

A balloon catheter was obtained by following the procedure of Example 3, except that the entire surface of the balloon part was subjected without any masking to the same surface treatment as in Example 3. The balloon catheter was tested for friction resistance and resistance to extraction by the methods depicted in FIGS. 5 and 6. The results are shown in Table 3.

TABLE 3

| Sample No. | Surface treatment | Covering ratio[1] | Friction resistance (gf)[2] | Resistance to extraction (gf)[3] |
|---|---|---|---|---|
| Example 3 | Partial treatment | 2.5 | 8.4 | 478 |
| Control 5 | None | — | 19.3 | 503 |
| Control 6 | Whole treatment | 5.7 | 7.9 | 233 |

[1]Amount of polymer bound per unit weight of substrate, expressed in terms of percent by weight.
[2]Value of resistance obtained immediately after completion of the last of a total of 100 strokes.
[3]Highest value of resistance found during extraction.

What is claimed is:

1. A vasodilating catheter balloon which comprises an inflatable balloon body which comprises tapered portions at both ends and a cylindrical portion between said tapered portions for dilating the interior of a blood vessel, said tapered portions comprise part of said inflatable balloon and are constituted of the same materials as the inflatable balloon body, wherein said balloon body has a lubricating portion formed on any one of said tapered portions and a non-lubricating portion on said cylindrical portion.

2. A balloon according to claim 1, wherein said balloon body has a leading end and said lubricating portion is formed on a tapered portion in the leading end of said balloon body.

3. The vasoldilating catheter balloon of claim 1 wherein the balloon when inflated comprises an inner tube through the balloon body and an outer tube connected with the interior at one end of the balloon body.

4. The vasodilating catheter balloon of claim 1 wherein the lubrication portion is formed at a position of the catheter which is subject to resistance open insertion of the catheter into a blood vessel.

5. The vasodilating catheter of claim 1 wherein the lubrication portion is formed of a polymeric substance capable of being dissolved with water to be absorbed.

6. A balloon according to claim 5, wherein said polymeric substance is made of at least one member selected from the group consisting of maleic anhydride type polymeric substance, acryl amide type polymeric substance and polysaccharides.

7. A balloon according to claim 6, wherein said acryl amide type polymeric substance is a polymer having N,N-dimethyl acryl amide as a main component thereof.

8. A balloon according to claim 6, wherein said maleic anhydride type polymeric substance is methyl vinyl ether-maleic anhydride copolymer.

9. The vasodilating catheter of claim 1, wherein the lubricating portion is formed of a polymeric substance capable of being swelled with water to be absorbed.

* * * * *

UNITED STATES PATENT AND TRADEMARK OFFICE
CERTIFICATE OF CORRECTION

PATENT NO. : 5,503,631
DATED : April 2, 1996
INVENTOR(S) : Makoto ONISHI et al

It is certified that error appears in the above-indentified patent and that said Letters Patent is hereby corrected as shown below:

In Column 5, line 12, delete "as-illustrated" and insert -- as illustrated --.
In Column 7, line 54, delete "(At," and insert -- (Ar, --.

Signed and Sealed this

Eleventh Day of June, 1996

Attest:

BRUCE LEHMAN

Attesting Officer  Commissioner of Patents and Trademarks